United States Patent
Sage, Jr. et al.

(10) Patent No.: US 9,907,904 B2
(45) Date of Patent: Mar. 6, 2018

(54) SPRING-DRIVEN DRUG DELIVERY DEVICE

(71) Applicants: Burton H. Sage, Jr., Escondido, CA (US); Gina G. Stetsko, San Diego, CA (US)

(72) Inventors: Burton H. Sage, Jr., Escondido, CA (US); Gina G. Stetsko, San Diego, CA (US)

( * ) Notice: Subject to any disclaimer, the term of this patent is extended or adjusted under 35 U.S.C. 154(b) by 0 days.

(21) Appl. No.: 15/490,821

(22) Filed: Apr. 18, 2017

(65) Prior Publication Data
US 2017/0326292 A1    Nov. 16, 2017

Related U.S. Application Data

(60) Provisional application No. 62/334,177, filed on May 10, 2016.

(51) Int. Cl.
*A61M 5/20* (2006.01)
*A61M 5/145* (2006.01)
(Continued)

(52) U.S. Cl.
CPC ........ *A61M 5/145* (2013.01); *A61M 5/14248* (2013.01); *A61M 5/14593* (2013.01);
(Continued)

(58) Field of Classification Search
CPC .............. A61M 5/145; A61M 5/14248; A61M 5/14593; A61M 5/158; A61M 5/16805;
(Continued)

(56) References Cited

U.S. PATENT DOCUMENTS 4,140,117 A    2/1979    Buckles et al.
4,552,561 A    11/1985   Eckenhoff et al.
(Continued)

FOREIGN PATENT DOCUMENTS

EP    2591815       5/2013
WO    2012/032411   3/2012
(Continued)

OTHER PUBLICATIONS

International Search Report received in PCT/US2017/028208, dated Jul. 20, 2017, 10 pages.

*Primary Examiner* — Kevin C Sirmons
*Assistant Examiner* — Tiffany Legette-Thompson
(74) *Attorney, Agent, or Firm* — Arc IP Law, PC; Joseph J. Mayo

(57) ABSTRACT

A drug delivery device or patch-like delivery device which employs a spring force and an inclined surface to apply pressure on a fluid reservoir, thereby delivering medicament to a user's body. The slope of the inclined surface may be engineered to control the drug delivery rate. The device may be low profile and wearable, for example in the form of a patch. A visual indicator of the amount of medicament delivered or remaining may be incorporated, for example via a transparent window that shows the progression of an inclined surface as it presses on the reservoir. The device may incorporate mechanisms for automatic extension and retraction of a cannula at the beginning and end of drug delivery. Drug delivery rate may be limited with flow restrictors, and by using a two-reservoir system with a viscous liquid displacing a reservoir containing the medicament.

15 Claims, 17 Drawing Sheets

(51) Int. Cl.
*A61M 5/158* (2006.01)
*A61M 5/142* (2006.01)
*A61M 5/168* (2006.01)

(52) U.S. Cl.
CPC ........ *A61M 5/158* (2013.01); *A61M 5/16804* (2013.01); *A61M 2005/14252* (2013.01); *A61M 2005/14506* (2013.01); *A61M 2005/1583* (2013.01); *A61M 2005/1585* (2013.01); *A61M 2205/583* (2013.01)

(58) Field of Classification Search
CPC ......... A61M 2005/14252; A61M 2005/14506; A61M 2005/1583; A61M 2005/1585; A61M 2205/583
USPC ........................................................ 604/138
See application file for complete search history.

(56) References Cited

U.S. PATENT DOCUMENTS

| | | | |
|---|---|---|---|
| 5,318,539 A | 6/1994 | O+Neil | |
| 5,318,540 A | 6/1994 | Athayde et al. | |
| 5,597,865 A | 1/1997 | Jackson | |
| 5,693,018 A | 12/1997 | Kriesel et al. | |
| 5,957,895 A | 9/1999 | Sage et al. | |
| 6,074,369 A | 6/2000 | Sage et al. | |
| 6,447,475 B1 | 9/2002 | Castellano | |
| 6,896,666 B2 | 5/2005 | Kochamba | |
| 7,250,037 B2 | 7/2007 | Shermer et al. | |
| 7,297,138 B2 | 11/2007 | Fangrow | |
| 7,300,419 B2 | 11/2007 | Fangrow | |
| 7,309,326 B2 | 12/2007 | Fangrow | |
| 7,311,694 B2 | 12/2007 | Fangrow | |
| 7,314,463 B2 | 1/2008 | Fangrow | |
| 7,331,939 B2 | 2/2008 | Fangrow | |
| 7,407,491 B2 | 8/2008 | Fangrow | |
| 7,678,079 B2 | 3/2010 | Shermer et al. | |
| 7,927,306 B2 | 4/2011 | Cross et al. | |
| 7,981,085 B2 | 7/2011 | Ethelfeld | |
| 8,109,912 B2 | 2/2012 | Alferness et al. | |
| 8,128,597 B2 | 3/2012 | Cross et al. | |
| 8,187,228 B2 | 5/2012 | Bikovsky | |
| 8,202,250 B2 | 6/2012 | Stutz | |
| 8,361,030 B2 | 1/2013 | Carter | |
| 8,430,848 B1 | 4/2013 | Dawrant | |
| 8,444,604 B2 | 5/2013 | Cindrich et al. | |
| 8,449,504 B2 | 5/2013 | Carter et al. | |
| 8,512,287 B2 | 8/2013 | Cindrich et al. | |
| 8,870,821 B2 | 10/2014 | Laufer | |
| 2004/0010207 A1 | 1/2004 | Flaherty et al. | |
| 2005/0197625 A1 | 9/2005 | Haueter et al. | |
| 2006/0122562 A1* | 6/2006 | Needle | A61M 5/1454 604/185 |
| 2008/0091149 A1 | 4/2008 | Laufer | |
| 2008/0215015 A1* | 9/2008 | Cindrich | A61M 5/14248 604/257 |
| 2009/0088682 A1 | 4/2009 | Cross et al. | |
| 2009/0259182 A1 | 10/2009 | Cross et al. | |
| 2012/0041338 A1 | 2/2012 | Chickering et al. | |
| 2012/0209185 A1 | 8/2012 | Kamen et al. | |
| 2014/0148761 A1 | 5/2014 | Rotem et al. | |
| 2014/0350470 A1* | 11/2014 | Gyory | A61M 5/14248 604/134 |
| 2015/0011976 A1 | 1/2015 | Vouillamoz et al. | |
| 2015/0051547 A1 | 2/2015 | Cefai | |
| 2015/0190569 A1 | 7/2015 | Nagel et al. | |

FOREIGN PATENT DOCUMENTS

| | | |
|---|---|---|
| WO | 2012/042517 | 4/2012 |
| WO | 2013/068900 | 5/2013 |
| WO | 2013/136327 | 9/2013 |

* cited by examiner

SPRING-DRIVEN DRUG DELIVERY DEVICE

This application claims the benefit of U.S. Provisional Patent Application 62/334,177, filed 10 May 2016, the specification of which is hereby incorporated herein by reference.

BACKGROUND OF THE INVENTION

Field of the Invention

One or more embodiments of the invention are related to the field of low profile drug delivery systems worn on the skin such as patch devices and/or patch device systems and/or adhesive patch devices and/or patch injection systems and the use of the same in methods for delivery of medicaments or therapeutic substances into tissue such as skin and/or muscle. More particularly, but not by way of limitation, one or more embodiments of the invention enable a spring-driven drug delivery device.

Description of the Related Art

There is a significant demand for the development of improved wearable drug delivery devices and/or systems for delivery of medicaments to the body. This observation is supported by the abundance and wide range of current drug delivery device designs currently in the field. However, there remains an unmet need for providing efficient drug delivery with a mechanical device that supports various delivery modes including for example a constant rate of infusion.

Syringe technology is well known and is the most common device for drug delivery. A basic syringe delivers its contents in a single bolus and the user typically attempts to minimize the elapsed time the needle pierces the skin. Indeed, often unappreciated for syringes, is the fact that the force available with a hand and thumb is only several pounds (lbs.), but the area of a plunger (especially in syringes and pen-type devices) is so small that the actual pressure in the fluid may well be over 100 lbs. per square inch.

Another variation of syringe technology is the syringe pump which functions to deliver contents over some extended period of time by moving the plunger of the syringe at a fixed or variable rate. Often, a syringe barrel is transparent so that quantitative aspects (amount, appearance, rate of delivery) of the drug solution can be assessed by the user.

Other variations of syringe technology include systems which mimic the performance of the basic syringe and syringe pump, however, because these systems are advantageously wearable and relatively low profile, the technology fails to provide the user with a strong enough source of driving force to administer an injection as a single bolus in a short period of time. Rather, these systems are designed to infuse drug solutions over a prescribed period of time. Additionally, these systems fail to provide the user with a visual of the drug solution before and/or during use.

Some wearable delivery devices and systems include a sliding interface such as a plunger sliding along the inside of a syringe barrel. However, such devices and systems suffer from a common issue known as slip-stick where the plunger motion is not uniform down the barrel. Slip-stick can cause inadvertent bolus delivery when the plunger is actuated after rest. It can cause the barrel to leap forward erratically when it finally moves because static friction is larger than sliding friction. This is also true in syringe pumps where rotary motion of the plunger driver motor is smooth, the motion of the plunger down the barrel is not smooth because of the changing frictional force of the plunger on the barrel.

U.S. Pat. Nos. 5,693,018; 5,957,895; and U.S. Pat. No. 6,074,369 describe devices which are low profile and can be worn on the skin more comfortably than a syringe. While such devices and systems are designed to overcome the common slip-stick issue, they do not provide a strong enough source of driving force to administer an injection as a single bolus in a short period of time. Additionally, they fail to provide the capability of variably controlled administration rates following diurnal or other desired administration chrono-pharmacological patterns. These devices and systems also do not provide the user with a visual indication of the drug solution so that the user can verify original contents, and whether such contents are flowing appropriately into the body from the concealed pouch from which they are contained.

In particular, U.S. Pat. No. 5,957,895; and U.S. Pat. No. 6,074,369 describe a design underpinned by the use of Belleville washers, which have an inherent non-constant force and which such force can only be minimized but not completely eliminated. U.S. Pat. No. 5,693,018 describes a design incorporating elastomeric members, which change shape as the reservoir housing the drug solution empties, and which reduce the desired force during drug delivery.

While many various delivery devices may be found, for example in U.S. Pat. Nos. 8,430,848; 8,449,504; 8,109,912; 7,927,306; 8,128,597; 8,361,030; 8,870,821; 8,187,228; 8,202,250; 7,407,491; 7,331,939; 7,314,463; 7,311,694; 7,309,326; 7,300,419; 7,297,138; 8,444,604; 8,512,287; 6,896,666; 7,678,079; 7,250,037; 7,981,085; 6,074,369; 6,447,475; 5,597,865 and 5,693,018; United States Application Numbers 2014/0148761; 2012/041338; 2009/0259182; 2009/0088682; 2008/0091149; and 2004/0010207; European Application Number 2591815 A1; and International Publication Numbers WO 2013/136327; WO 2013/068900; WO 2012/042517; and WO 2012/032411; none of these references disclose the embodiments of the delivery device disclosed herein.

Therefore, the drug delivery device disclosed herein provides innovative improvements and several advantages in the field of drug delivery because the novel design of the device disclosed herein provides the capability of delivering a drug solution efficiently and quickly for a bolus injection and also provides the capability for delivering a drug solution at a variably controlled constant rate for infusion.

All documents and references cited herein and in the referenced patent documents, are hereby incorporated herein by reference.

For at least the limitations described above there is a need for a spring-driven drug delivery device.

BRIEF SUMMARY OF THE INVENTION

One or more embodiments described in the specification are related to a spring-driven drug delivery device. Embodiments of the invention enable a drug delivery device, such as a low profile patch wearable on the user's skin, capable of delivering medicament at a desired constant or variable rate. Embodiments of the drug delivery device disclosed herein may deliver medicaments at a rate which is a rapid or prolonged constant rate or a variable rate where drug solution is delivered in either a diurnal manner or some other desired function of time. The device disclosed herein is also capable of delivering a loading dose of drug which is then followed by a prolonged delivery rate of the drug.

One or more embodiments of the invention may include a device for delivering medicament to a user's body. The device may have a medicament containment reservoir with an inner cavity that contains a fluid incorporating one or more medicaments. The outer surface of the reservoir may be capable of being placed under mechanical pressure. The device may have a cannula that contacts the body, and a flow path for conveying the medicament from the reservoir to the cannula and into the body. The device may include a source of force for exerting pressure on the reservoir to cause medicament to flow along the flow path; the source of force may for example include one or more springs. A force transmission member may transmit this force from the source to the outer surface of the reservoir. This force transmission member may have an inclined surface that contacts an inclined surface follower coupled to the outer surface of the reservoir. Force from the source may generate motion of the force transmission member, which causes the inclined surface to move relative to the inclined surface follower; motion of the inclined surface exerts a force on the outer surface of the reservoir. This force on the outer surface may generate pressure on the fluid contained in the inner cavity of the reservoir, which causes the fluid to flow on the flow path to the cannula and into the body.

In one or more embodiments, the force transmission member may include a wedge. In one or more embodiments, the force transmission member may include a screw.

The slope of the inclined surface of the force transmission member may be engineered to generate any desired rate of drug delivery. For example, without limitation, it may be engineered to generate a relatively constant force on the outer surface of the reservoir over a portion of the motion of the force transmission member, which results in a relatively constant rate of drug delivery. In one or more embodiments, the spring force driving the force transmission member may vary over time (for example, it may decrease as the spring returns towards its equilibrium position, per Hooke's Law). The inclined surface may be engineered to compensate for this decreasing spring force, such that the overall force on the reservoir remains relatively constant even as the spring force decreases.

In one or more embodiments, the device may include a cannula deployment assembly that deploys the cannula outside the device during drug delivery and retracts the cannula inside the device after drug delivery. In further embodiments, the inclined surface may be operably connected to the cannula deployment assembly, wherein the source of force causes force transmission member with the inclined surface to move. Motion of the force transmission member may for example include a cannula extension motion, followed by a medicament delivery motion, followed by a cannula retraction motion.

In one or more additional embodiments, at least a portion of the inclined surface of the device may be visible through a transparent viewing window. The viewing window may have indicator markings showing status of the delivery of the medicament or operation of the device. The device may also have indicator markings on the back of a moving member that, through the inclined surface follower, applies force to the reservoir. These indicators or markings may provide visual indicators of the amount of medicament that has been delivered, or the amount of medicament remaining in the reservoir.

In one or more embodiments, the device may be low-profile, wearable, adhesive, or a combination thereof. In one or more embodiments, the device may have a housing that contains device components such as the reservoir, the force transmission member, and the spring. The housing may be configured to be worn on the user's skin, for example as a patch device. In one or more embodiments, the housing may have a low-profile, for example with a relatively low height compared to its width and length along the user's skin.

In one or more embodiments, the inclined surface of the device may include the profile of a linear cam, wherein the inclined surface may have varying slopes such that the pressure in the reservoir is constant, which results in an essentially constant delivery rate.

In one or more embodiments, the device may include a flow resistor that limits the rate at which fluid flows along the flow path into the user's body. A flow resistor may for example be used for extended delivery of a medicament over a long period of time.

In one or more embodiments, a medicament containment reservoir system may include a first reservoir and a second reservoir, where the second reservoir comprises additional medicament, and a flow path and force system (which may include an inclined surface) for conveying the medicament from either reservoir system to the body.

In one or more embodiments, the device may have a first reservoir containing a medicament, and a second reservoir that contains an auxiliary fluid that may be used to apply force to the first reservoir. For example, the first reservoir may have a rigid outer shell and an inner liner that is not coupled to the outer shell, which separates the inner cavity of the reservoir from a secondary chamber between the rigid outer shell and the inner liner. The device may have flow path between the second reservoir and the secondary chamber of the first reservoir. The force transmission member may apply force to the second reservoir, which causes the auxiliary fluid to flow into the secondary chamber of the first reservoir; this applies pressure to the liner and forces the medicament along the flow path towards the body. The flow path between the second reservoir and the secondary chamber of the first reservoir may incorporate a flow restrictor. In one or more embodiments, the auxiliary fluid may be more viscous than the fluid containing the medicament.

One or more embodiments of the invention enable a method of delivering medicament to a patient, the method comprising: providing a device disclosed herein to the patient, instructing the patient to wear the device, and instructing the patient to actuate the device, thereby triggering the source of force configuration to move the inclined surface to an actuated position, thereby urging the medicament from the reservoir along the flow path to the patient's body.

Also, disclosed herein is a kit comprising the device disclosed herein and a cannula for operable use therein. Additionally, disclosed herein is a kit comprising the device disclosed herein and instructions for use thereof. Also, disclosed herein is a kit comprising the device disclosed herein and a vial or container of medicament for delivery using the device thereof.

Additionally, disclosed herein are methods and kits for manufacture and/or delivery and/or deployment of the delivery device or patch device disclosed herein.

In other embodiments, the delivery device in the preceding paragraphs may incorporate any of the preceding or subsequently disclosed embodiments.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION OF THE INVENTION

Figure 1:
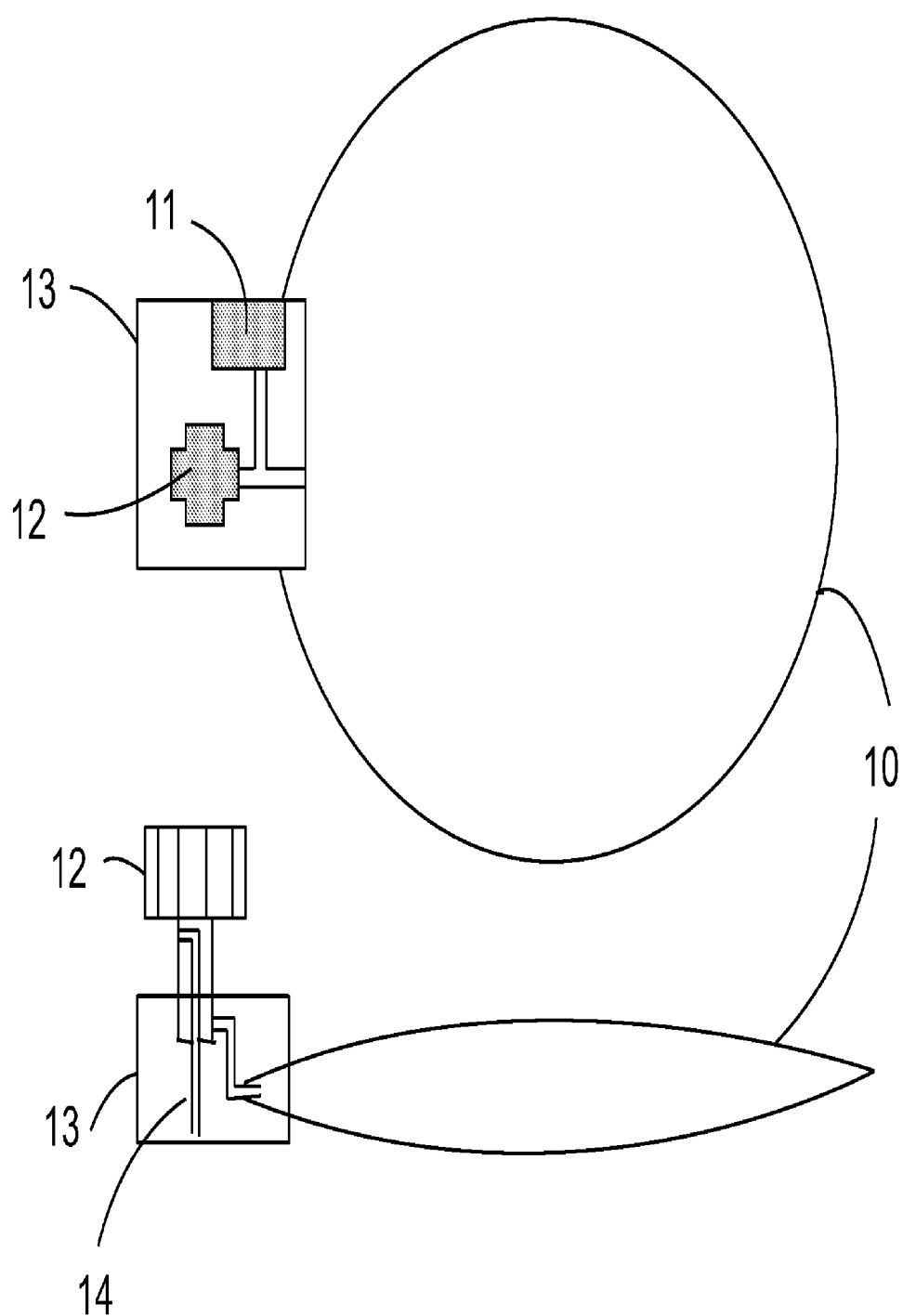
FIG. 1 illustrates perspective views of an embodiment of a delivery device disclosed herein showing a medicament containment reservoir in the full state.

A spring-driven drug delivery device will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

The delivery device disclosed herein is illustrated in the drawings and description in which like elements are assigned the same reference numerals. However, while particular embodiments are illustrated in the drawings, there is no intention to limit the delivery device disclosed herein to the specific embodiment or embodiments disclosed. Rather, the delivery device disclosed herein is intended to cover all modifications, alternative constructions, and equivalents falling within the spirit and scope of the invention. As such, the drawings are intended to be illustrative and not restrictive.

Unless otherwise defined, all technical terms used herein have the same meaning as commonly understood by one of ordinary skill in the art to which this technology belongs.

Exemplary embodiments of the delivery device disclosed herein are depicted in FIGS. 1-17.

For the purposes of the delivery device disclosed herein, the terminology "corresponds to" and/or "in operable connection with" means there is a functional and/or mechanical relationship between objects and/or mechanisms and/or members and/or components of and/or within the delivery device which correspond to each other. For example, a delivery device component such as a cannula deployment system corresponds to (or is compatible with) and/or is in operable connection with an inclined surface component or member of the device in the context of deployment thereof.

For the purposes of the delivery device disclosed herein, the terminology "delivery device" means and/or may be interchangeable with terminology such as, without limitation, "device" or "delivery device system" or "delivery system" or "system" or "delivery patch device" or "patch" or "patch system" or "delivery device patch system" and the like.

For the purposes of the delivery device disclosed herein, the terminology "reservoir system" means and/or may be interchangeable with terminology such as, without limitation, "reservoir subsystem" or "reservoir" or "system" or "subsystem" or "medicament-containing reservoir" or "fluid-containing reservoir" or and the like.

For the purposes of the delivery device disclosed herein, the terminology "driving system" means and/or may be interchangeable with terminology such as, without limitation, "force delivery system" or "system" or "force delivery subsystem" or "delivery subsystem" or "subsystem" or "driver" or "force driver" and the like.

For the purposes of the delivery device disclosed herein, the terminology "inclined surface" means and/or may be interchangeable with terminology such as, without limitation, "wedge" or "ramp" or "wedge member" or "ramp member" or "inclined surface member" or "member" and the like.

The delivery device and/or patch disclosed herein may be configured to overcome a burdensome and significant limitation in the field of delivery devices. The principle of Hooke's law, in such devices where the source of energy is a spring or spring-like component designed to force medicament or fluid from a reservoir, states that the force provided by the spring component changes in a linear fashion as the spring returns from its initial loaded position to its relaxed position. In this spring-driver delivery device context, Hooke's law is true for spring components such as, without limitation, extension springs, spiral springs, compression springs, torsion springs, watch springs and the like including elastomeric springs such as in U.S. Pat. No. 5,693,018. Therefore, as the spring component applies the force to deliver the drug, the amount of force provided by the spring decreases which can often lead to non-constant delivery and/or poor control.

Figure 2:
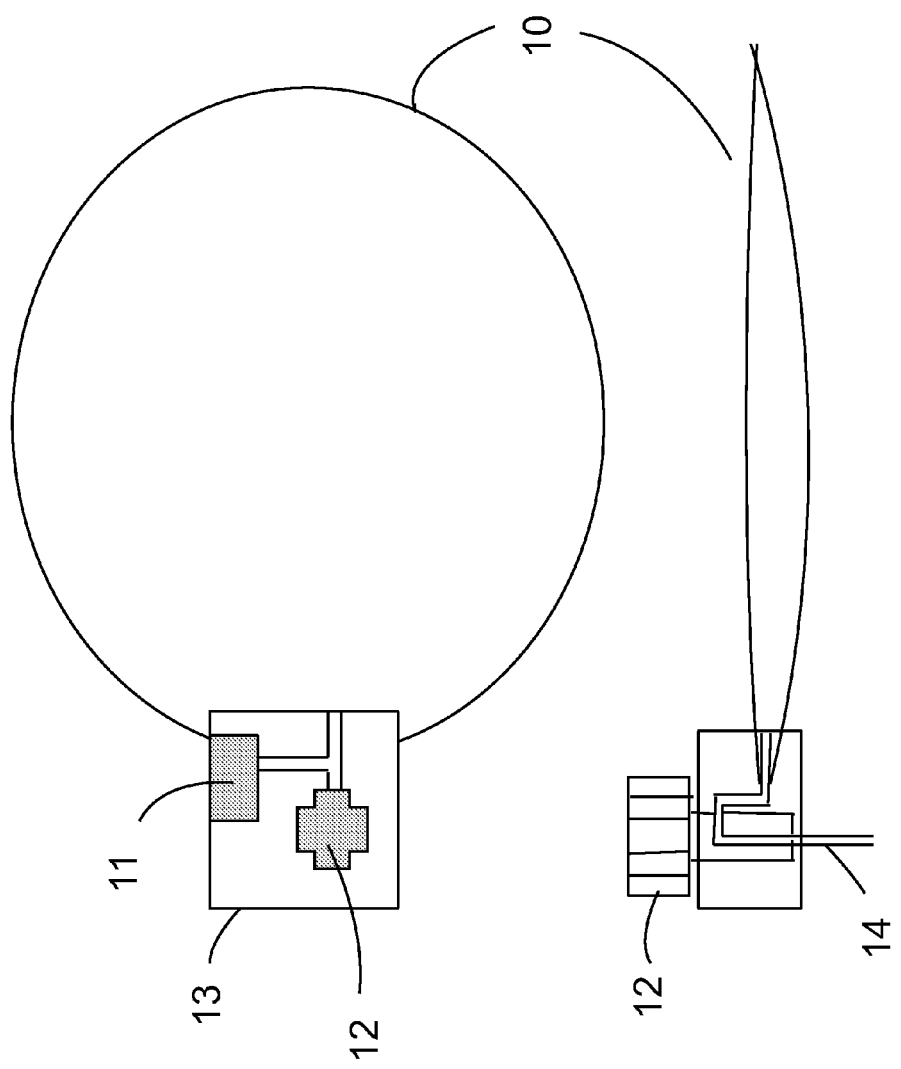
FIG. 2 illustrates a perspective view of an embodiment of a delivery device disclosed herein showing a medicament containment reservoir in the partially full state.
Figure 3:
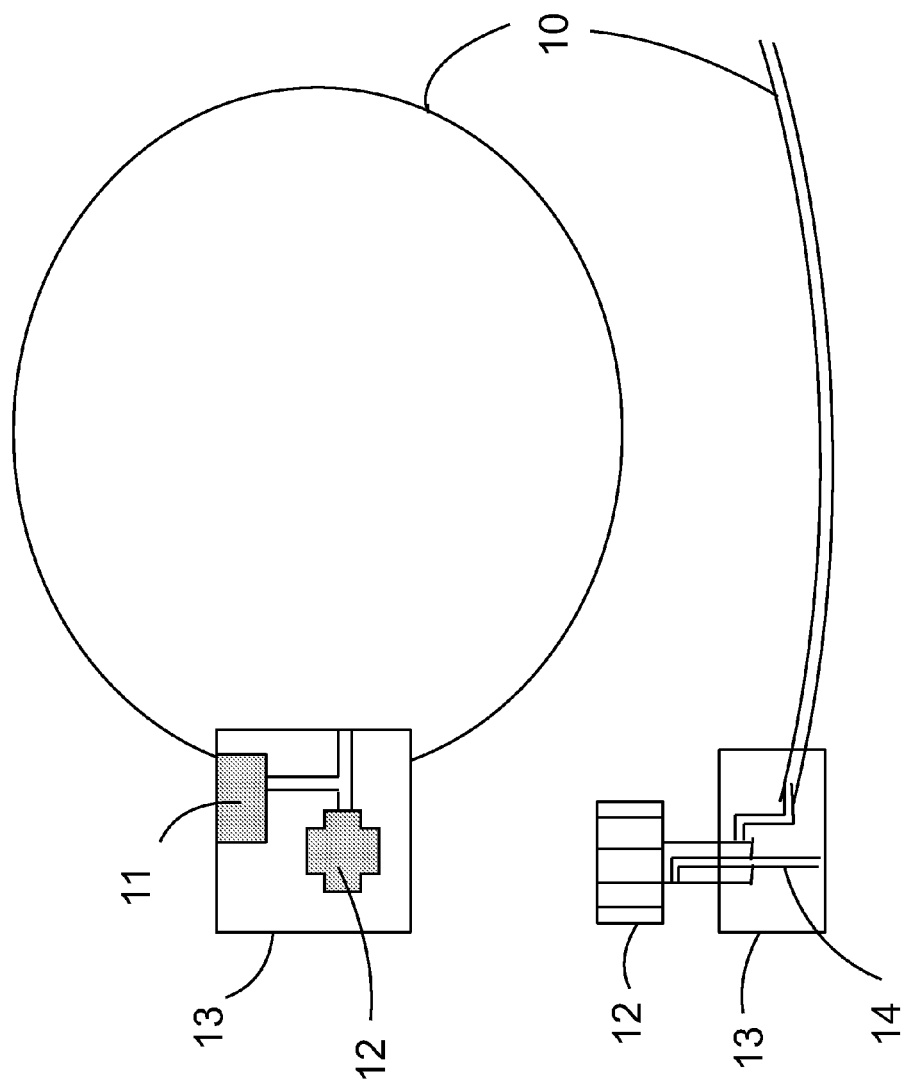
FIG. 3 illustrates perspective views of an embodiment of a delivery device disclosed herein showing a medicament containment reservoir in the depleted state.

The delivery device and/or patch disclosed herein may comprise a novel configuration which overcomes Hooke's Law and the inherently small amount of force available to such spring components (in the aspect where the source of energy is a spring component designed to force medicament from a reservoir). Foundationally, the delivery device and/or patch disclosed herein may comprise the following two subsystems: 1) the reservoir system, and 2) the driving system. These two subsystems may be contained in a device case, for example in a low-profile patch-like housing or encasement. An exemplary patch-like housing is shown in FIG. 1, wherein the reservoir system comprises a 10 reservoir which is in a "filled" status, in that it contains the desired and/or required volume of medicament or drug solution or fluid to be delivered to the user or patient. The reservoir system comprises a 10 medicament-containing reservoir which is fillable through a 11 fill port. The patch-like 13 housing comprises the flow path which is a path running from the 11 fill port to the 10 reservoir and from the 10 reservoir to the patient through the needle assembly and 14 cannula. FIG. 1 shows the embodiment of the flow path and additionally shows the blockage of the 10 reservoir to the 14 cannula so that the reservoir is sealed. Such a 10 reservoir and/or reservoir system can be made from a variety of readily available materials which function with the mechanical strength to contain fluid, maintain fluid in a sterile and non-contaminated state, and prevent the evaporation or leakage of fluid or its solvent. In one embodiment, the 10 reservoir is also made of flexible material which is capable of moving from a full condition as shown in FIG. 1 to a completely collapsed condition as shown in FIG. 3. FIG. 2 also shows the 10 reservoir system after the flow path from the 10 reservoir to the 14 cannula (and to the user/patient) once the delivery device disclosed herein is actuated and is in the process of delivering medicament. In this exemplary embodiment of FIG. 2, the 12 needle assembly is rotated such that the flow path from the 10 reservoir (which is shown to be partially collapsed as the medicament has flowed out of the reservoir) is open to the 14 cannula and the 14 cannula has been moved from a position within the device or patch to a position where the cannula has moved outside the device case and is in position to have entered the skin of the user if the device had been placed on a patient. FIG. 3 shows an embodiment wherein the reservoir system is complete after delivery of the medicament. In this scenario, 12 needle assembly rotates again so that the 14 cannula is once again back inside the device and the 10 reservoir collapses indicating its empty condition/status. Such materials for function of fluid containment in a 10 reservoir or reservoir system may include for example, without limitation, poly-olefins such as polyethylene. In another embodiment, one wall of the 10 reservoir is rigid and one wall is flexible. Although rigidity and flexibility are dependent on material thickness, materials capable of rigidity may include, for example and without limitation, thermoplastics such as polycarbonate. Materials capable of flexibility may include, for example and without limitation, spring metals such as stainless steel.

Figure 4:
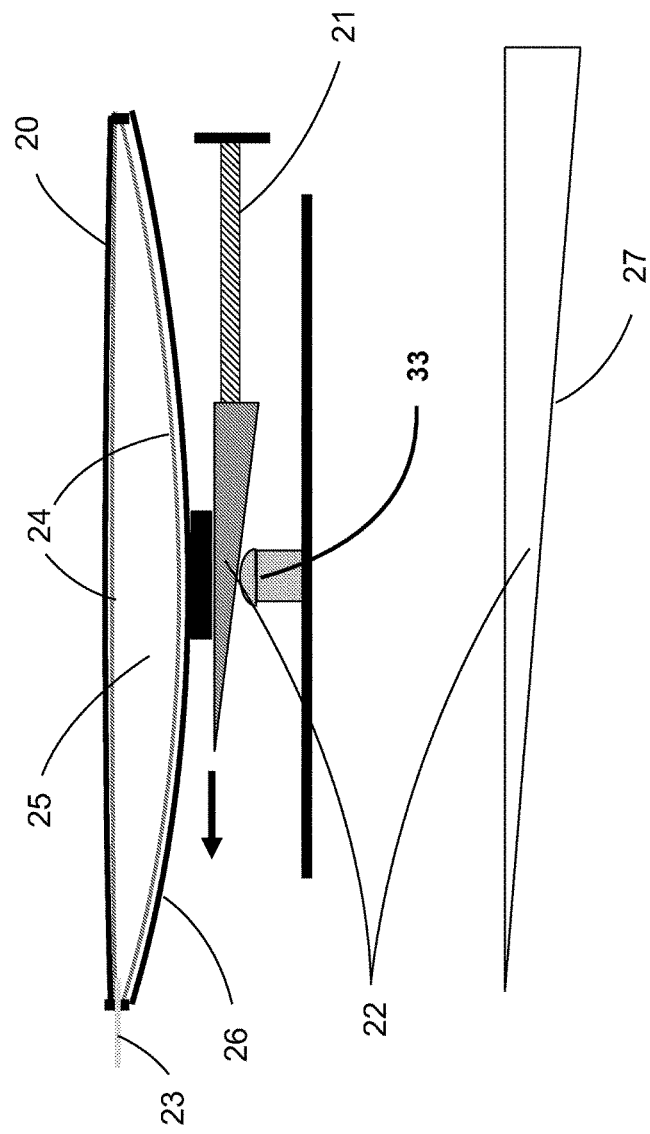
FIG. 4 illustrates perspective views of an embodiment of a delivery device disclosed herein showing an inclined surface comprising a constant slope.
Figure 5:
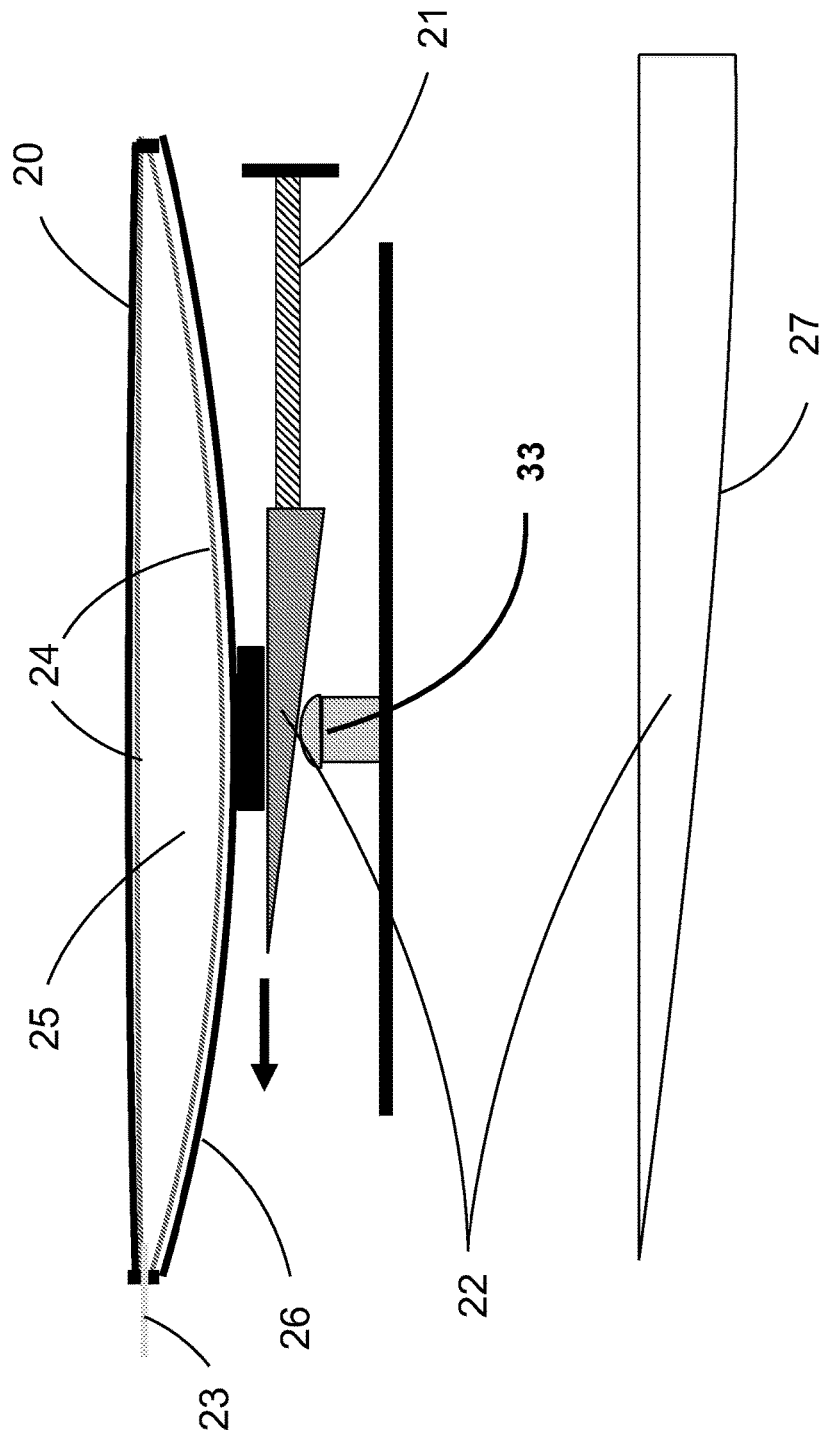
FIG. 5 illustrates a perspective view of an embodiment of a delivery device disclosed herein showing an inclined surface comprising a variable slope.

The delivery device disclosed herein and illustrated in the Figures may comprise a novel configuration of an inclined surface orientated between a spring component and a medicament-containing 25 reservoir, as illustrated in FIG. 4. Such an inclined surface may be part of the driving system (or force delivery system) of the device or patch disclosed herein. Indeed, the 25 reservoir system disclosed herein may be driven by the spring-pushing 22 wedge (or inclined surface) of the force delivery system. FIG. 4 shows an exemplary schematic of an embodiment of a force delivery or driving subsystem. Such a configuration overcomes the limitations described above related to Hooke's Law and often associated with a spring-based source of force (in the aspect of devices where the source of energy is a spring component designed to force medicament from a 25 reservoir or pouch). In an embodiment, the medicament-containing 25 reservoir may be, for example, lined with a 24 biocompatibility liner. In one embodiment, the 20 upper outer member of the reservoir may be rigid, and may be made of material such as, without limitation, polycarbonate, and the 26 lower outer member may be made of a material, such as for example, without limitation, stainless steel. As the 21 spring component pushes the 22 wedge, wherein the 22 wedge contacts 33 an inclined surface follower coupled to the outer surface of the 25 reservoir, the 22 wedge moves relative to 33 the inclined surface follower and the 26 lower reservoir member is pushed towards the 20 upper outer member thereby emptying the 25 reservoir (through the 23 outlet). The 27 shape (contour) of the 22 wedge (or inclined surface) determines the rate at which the 25 reservoir is emptied since the 23 outlet may also serve as a 29 flow resistor or flow restrictor. Indeed, the inclined surface (or 22 wedge) is capable of being implemented with a constant (any) slope, or a slope engineered to affect a desired delivery rate. A certain 27 shape, as derived and/or designed through the formulas below, will permit constant flow of the medicament through the 23 outlet tube. Other 27 shapes will permit other alternative and/or variable flow versus time profiles. An embodiment exemplified in FIG. 4 shows the 22 wedge (or inclined surface) with a slightly concave profile. FIG. 5 shows the 22 wedge with a convex profile. A linear profile and/or additional shapes of the 22 wedge can also be selected as per the desired time profile of the delivery of the medicament.

The relationship between source of force and the inclined surface in the embodiment of FIG. 4 can be described in mathematical terms as follows:

When "W" is the force on the 25 reservoir, "S" is the force exerted by the 21 spring, "θ" is the slope of inclined surface, and "C" is coefficient of friction, then $$W=S*\mathrm{Cos}(\theta)/(\mathrm{Sin}(\theta)+C*\mathrm{Cos}(\theta)).$$

In an embodiment of the delivery device or patch disclosed herein, when the angle of the inclined plane is small, as shown in FIG. 4, $\mathrm{Cos}(\theta)$ is approximately 1 and $\mathrm{Sin}(\theta)$ is approximately $\theta$, the relationship is shown as $$W=S/(\theta+C).$$

In another embodiment of the delivery device or patch disclosed herein, when the delivery of the medicament from the 25 reservoir is constant (based on the constant inclined surface), then the force on the reservoir, W, is essentially constant. Hence, the slope, θ, is directly calculated as a function of the spring force, S, as follows:

$$\theta=(S-WC)/W.$$

The delivery device and/or patch disclosed herein comprises a novel configuration comprising a "slope profile" which is key to obtaining the desired drug delivery rate profile (amount delivered per unit time). Referring to FIG. 4, for example, and specifically 22 wedge (inclined surface), as the 22 wedge is pushed to the left, drug solution is forced out of the 25 reservoir as the 22 wedge applies force to the 26 bottom of the 25 reservoir. The rate at which the drug solution is forced out depends on the force provided by the 21 spring and slope of the lower 27 surface of the 22 wedge. If the lower surface is parallel to the top surface of the 22 wedge, no drug would be forced out. Accordingly, the "slope profile" relates to the thickness of the 22 wedge as it varies from the thin tip on the left to the thicker section on the right. This thickness variation from left to right is what is referred to in this invention as the "slope profile." The slope profile can be made in essentially an infinite number of variations and based on the guidance herein, drug delivery devices of the invention disclosed herein can be calculated according to the equations disclosed herein with a preferred slope profile to suit the required and/or desired drug delivery variables relevant to the patient as well as to the properties of the medicament to be delivered. One slope profile, for example, provides an essentially constant rate of delivery. Such a slope profile providing an essentially constant rate of delivery by providing constant pressure on the drug solution or on the 25 reservoir holding the drug solution or medicament. With respect to the slope profile of this embodiment, as the driving 21 spring loses force, it relaxes towards its unconstrained shape, thereby providing a delivery device or patch with an essentially constant rate of delivery.

In another embodiment of the delivery device or patch disclosed herein, when the 26 pressure plate is a relatively stiff metal member, the pressure plate flexes like a drumhead to cause essentially complete delivery of the medicament from the 25 reservoir and applies its own force to the 25 reservoir. This force decreases as the drug solution is delivered from the 25 reservoir. In this embodiment, the slope, θ, is designed in a manner wherein the calculation compensates for the decreasing force and still provides an essentially constant pressure on the fluid in the 25 reservoir. As such, when the coefficient of friction, C, is small, and the slope, θ, is small, the force on the reservoir, W, is many times the force available from the 21 spring. In an additional embodiment, the slope, θ, is made variable over the length of the inclined surface and in this manner, the changes in force inherent in the 21 spring and the 25 reservoir are accommodated for in order to achieve the desired rate of delivery of the medicament as the 25 reservoir empties.

In another embodiment, the delivery device or patch disclosed herein provides for automatic deployment and retraction of the 12 needle or 14 cannula for piercing the skin of the user. In this regard, a needle deployment and retraction mechanism may be connected with the inclined surface. In one aspect of the needle deployment and retraction mechanism, the inclined surface is at an initial position and the cannula is retracted in a position inside the drug delivery device before delivery of the medicament begins. When the device is activated and before the medicament is released from the 10 reservoir, the inclined surface moves to exert force on the 10 reservoir. In the early stages of this motion of the inclined surface, the deployment and retraction mechanism engages with a portion of the inclined surface, causing the 14 cannula (or 12 needle) to be deployed. Once the 14 cannula is deployed, the inclined surface exerts force on the 10 reservoir to cause the medicament to be delivered to the user. Once delivery is complete, a second portion of the inclined surface engages with the needle deployment and retraction mechanism and the 14 cannula is retracted. In this way, once the device is placed on the body or adhered to the skin of the user, the activation of the device by the user may cause needle deployment, medicament delivery, and needle retraction. All these actions may be accomplished by the user without the direct action by the user to pierce his or her skin, or directly visualizing the 12 needle at any time point during the actuation and operation of the device.

Figure 6:
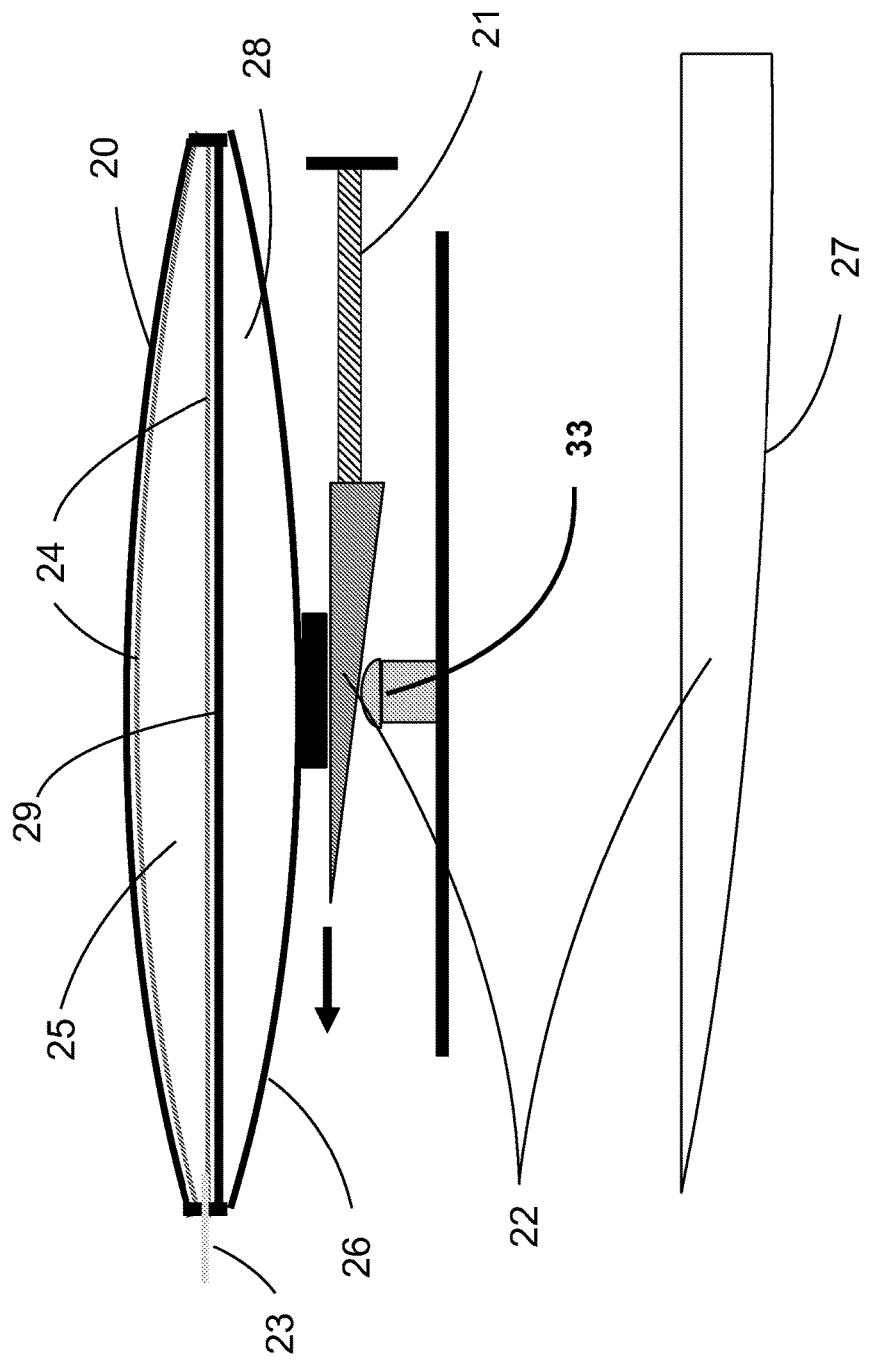
FIG. 6 illustrates a perspective view of an embodiment of a delivery device disclosed herein showing an inclined surface comprising a slope for delivery of a medicament over a prolonged period of time.
Figure 7:
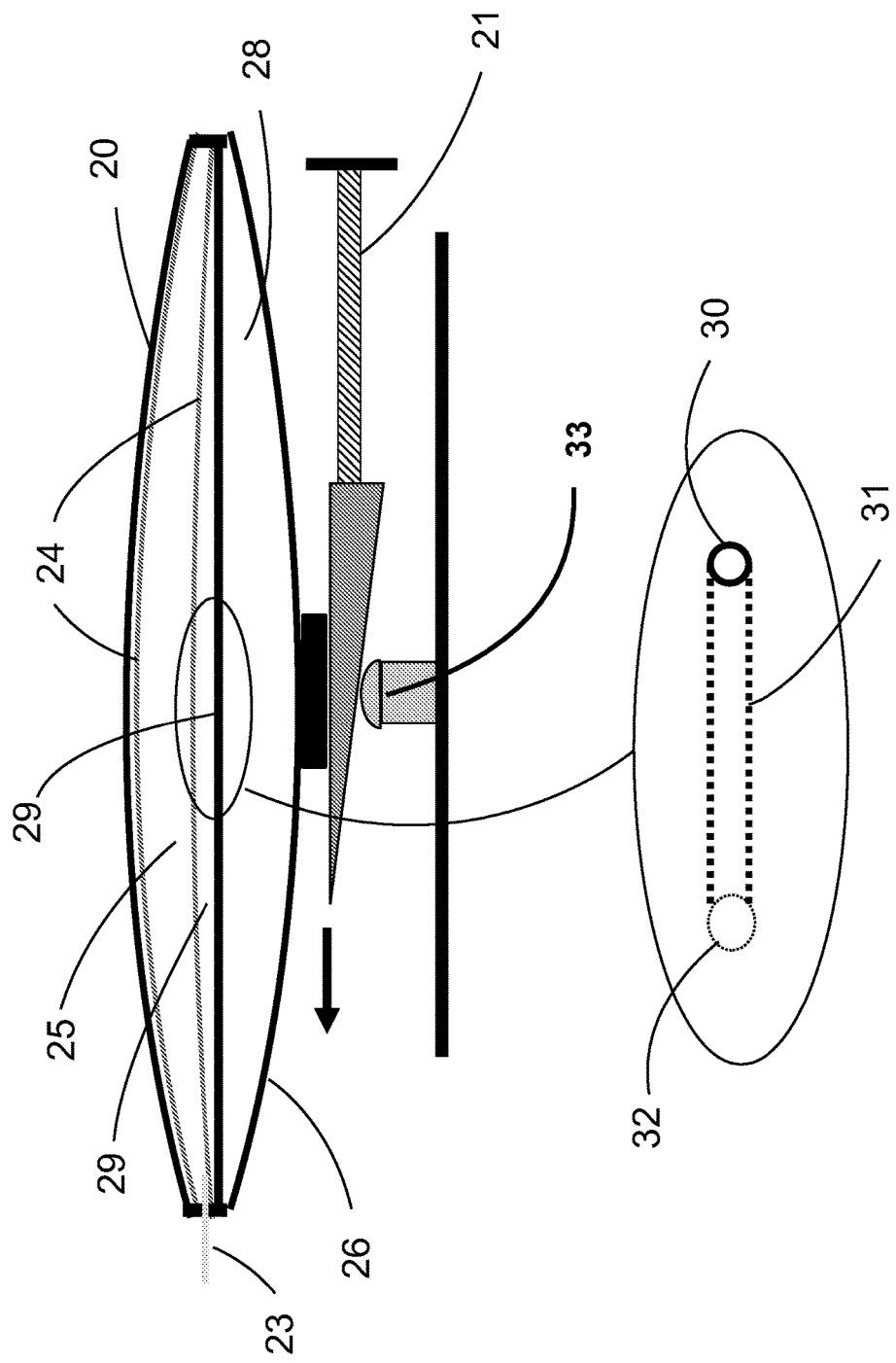
FIG. 7 illustrates a perspective view of an embodiment of a delivery device disclosed herein (and shown in FIG. 6) showing the magnified perspective view of the location of a flow resistor comprising within the flow path of the device.

In one or more embodiments, the delivery device or patch disclosed herein may possess the capability to deliver medicament or drug solutions at a constant rate over relatively long periods of time. In one or more additional embodiments, a 29 flow resistor is incorporated in the flow path to reduce the rate at which the medicament flows into the body, as illustrated in FIGS. 6 and 7. The 29 flow resistor—flow path configuration works well for relatively short periods of time up to about an hour for most medicaments or drug solutions having a viscosity close to that of water. In one or more embodiments, particularly suited for longer periods of time, a 28 second reservoir may be incorporated into the delivery device or patch so that it works in conjunction with the medicament-containing 25 reservoir. FIGS. 6 and 7 show the delivery device or patch disclosed herein configured with a 28 second reservoir. The 28 second reservoir may contain a separate fluid (auxiliary fluid) with a relatively high viscosity, and may be isolated from the medicament-containing 25 reservoir so that there is no fluid connection between the interiors of the two reservoirs. Rather, the fluid from the second reservoir flows through a 29 flow resistor in such a manner so that a force is exerted on the 25 first reservoir. When the patch is activated (or device is actuated), the driving force is applied to the 28 second reservoir. The fluid in the 28 second reservoir flows through the 29 flow resistor to exert force on the 25 first reservoir in such a manner so that the medicament is displaced or emptied from the 25 first reservoir. As the flow of the fluid out of the 28 second reservoir is at a desired drug delivery rate, and as it displaces the medicament of equal volume, the rate of delivery of the medicament equals the flow rate of the fluid in the 28 second reservoir. Since the rate of flow of the fluid in the 28 second reservoir is determined by the slope of the inclined surface, a variety of flow profiles can be created. The flow path functioning as a 29 flow resistor is shown in greater detail in FIG. 7.

FIG. 7 shows this embodiment of the drug delivery patch after delivery of the medicament begins. The 21 spring moves the 22 wedge (inclined surface or ramp) to the left, thereby causing the auxiliary fluid to leave the 28 second reservoir through the flow path. The flow path may be constructed with one or more pinholes and/or may be 29 flow resistors of a selected size to regulate the flow of the auxiliary fluid from the 28 second reservoir at a desired rate. Depending on the desired rate of flow, one may adjust either the size of the pinholes, or the diameter and length of the 29 flow resistor, or the viscosity of the auxiliary fluid, or any combination thereof. For example, as the term (time period) of the desired flow increases, the viscosity of the auxiliary fluid would need to increase, the size or number of pinholes would need to decrease, the length of the 29 flow resistor would need to increase, the diameter of the 29 flow resistor would need to decrease, and/or any combination thereof. FIG. 7 also shows the flow path as a 29 flow resistor with an 30 opening exposed to the reservoir, an 32 additional opening exposed to the reservoir, and a 31 flow resistor length. Some of the auxiliary fluid flows through the flow path into a space between the bottom of the 25 first reservoir element outer wall and the lower 24 biocompatibility member. This reduces the volume of the 25 reservoir, thereby forcing a portion of the medicament through the 23 exit port.

Figure 8:
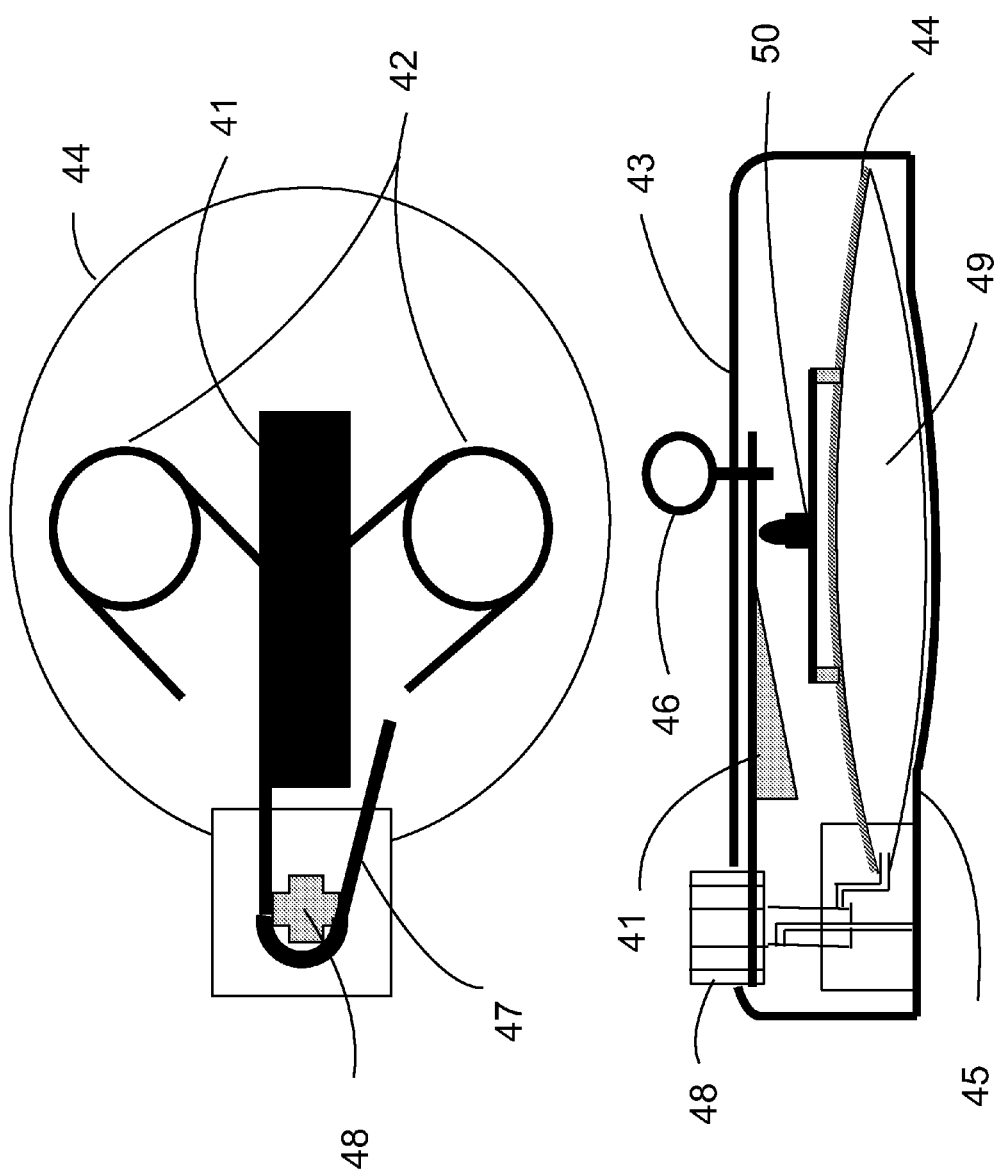
FIG. 8 illustrates a perspective view of an embodiment of a delivery device disclosed herein showing a source of force configuration comprising torsion springs.
Figure 9:
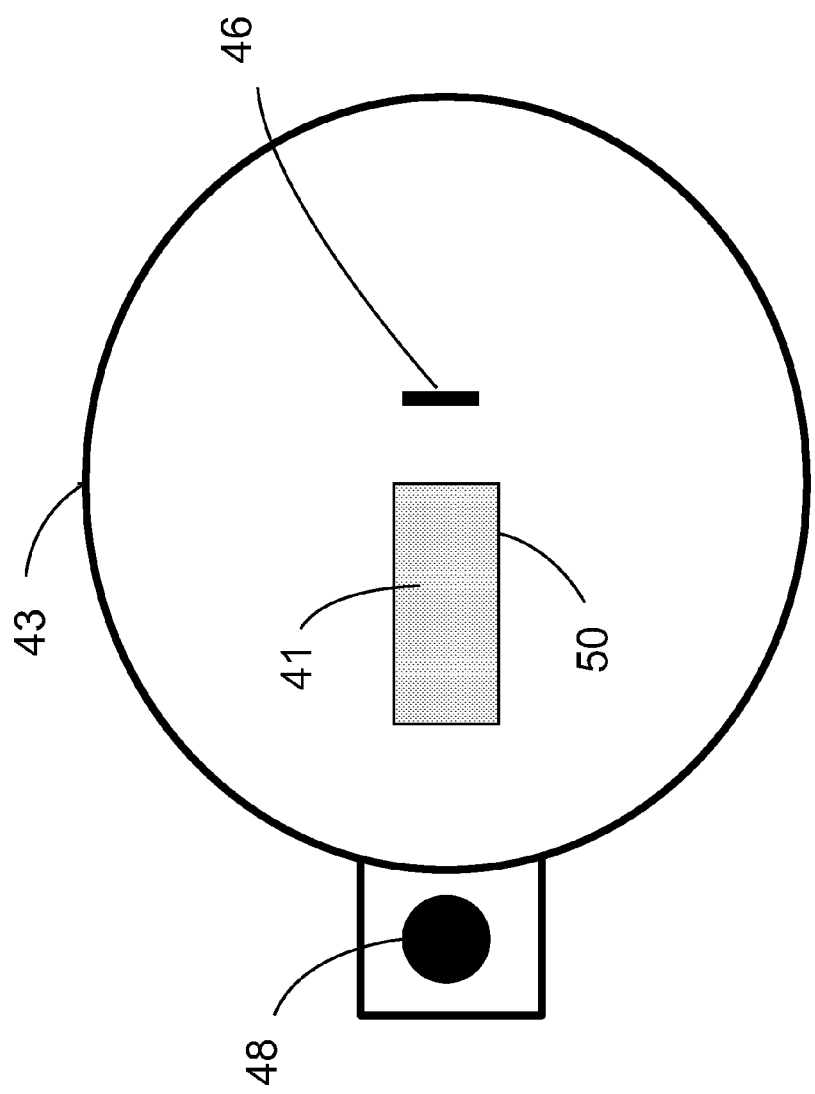
FIG. 9 illustrates an embodiment of a delivery device disclosed herein showing a perspective view of when the device is ready for activation.

FIG. 8 shows an alternative embodiment of the device or patch disclosed herein, wherein the driving force is supplied by 42 torsion springs which are positioned to drive 41 wedge member (inclined surface) to the right. The 41 wedge further extends to the left as a 47 extension to wrap around the 48 needle assembly. The 43 casing, in this embodiment, is transparent so that the user can observe the upper surface of the 41 wedge. When the 41 wedge member moves to the right, it will cause 50 pressing member to press against the 49 reservoir thereby putting pressure on the medicament. If the flow path shown in the 48 needle assembly were open, then the medicament would leave the 49 reservoir. However, 46 pin holds the 41 wedge member in place until the user desires administration of the medicament. The 44 top and 45 bottom of the reservoir are also shown herein. FIG. 9 shows the low profile outside of a delivery device or patch disclosed herein as it would appear to a user when it has been placed on the body. In this embodiment, the 46 pin is ready for pulling, and the back of the 41 wedge (inclined surface) is seen as a green band which indicates to the user that the low profile patch is ready for use.

Figure 10:
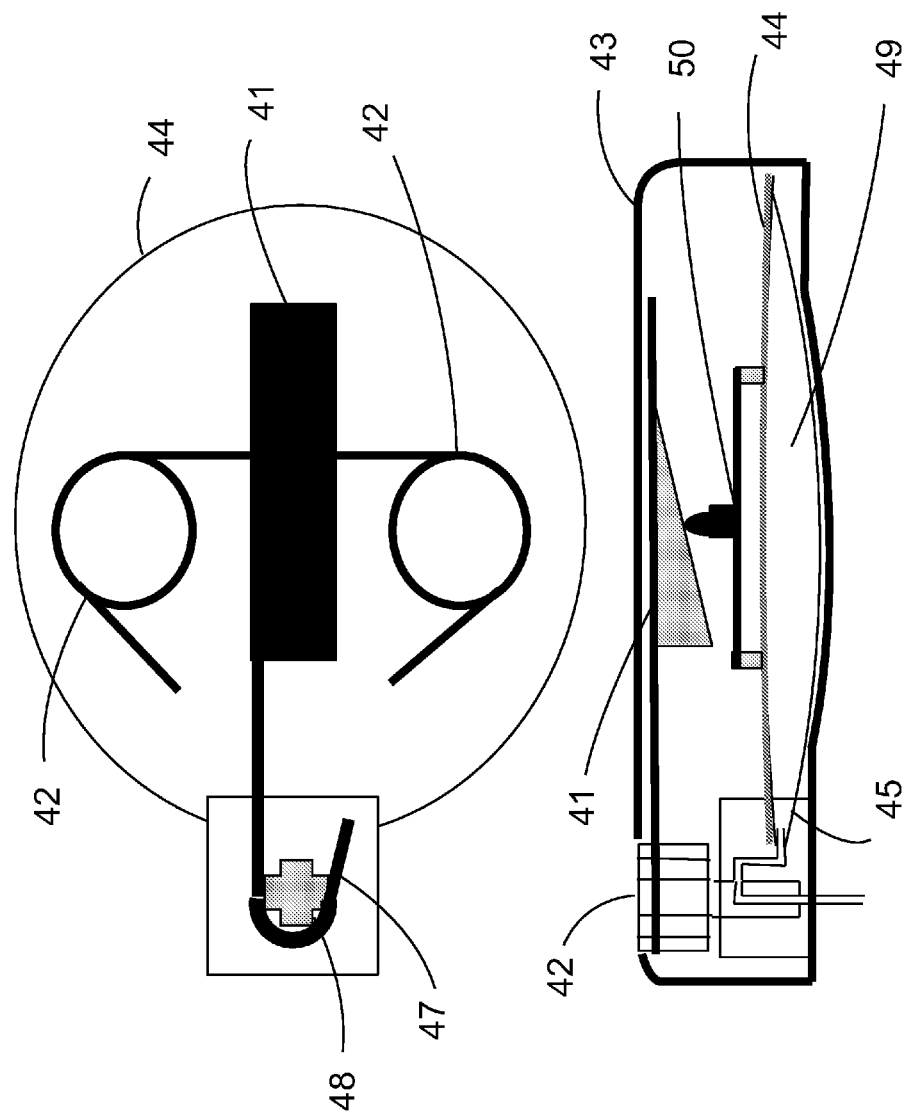
FIG. 10 illustrates a perspective view of an embodiment of a delivery device disclosed herein showing a source of force configuration comprising torsion springs. In this perspective view, about half of the medicament has been delivered.
Figure 11:
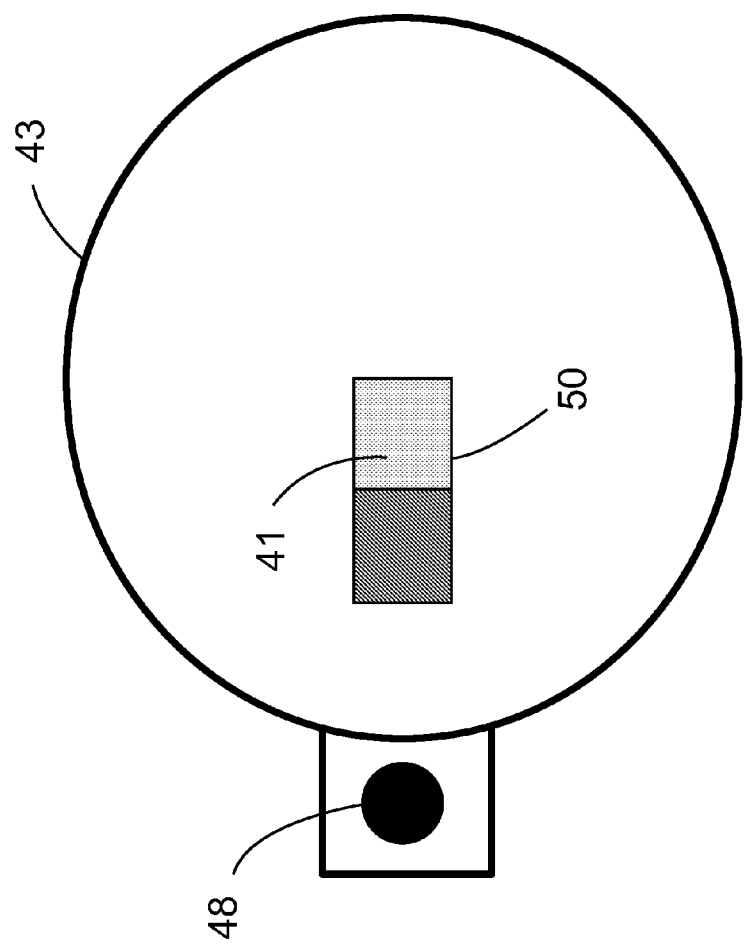
FIG. 11 illustrates a perspective view of an embodiment of a delivery device disclosed herein (and shown in FIG. 8) when about half the medicament is delivered.

FIG. 10 shows an embodiment of a delivery patch disclosed herein after it has been activated and a portion of the medicament has been administered. 42 torsion springs have moved the 41 wedge to the right and the 50 pressing member has compressed the 49 reservoir. As the 41 wedge moved to the right, the 47 wedge extension member rotated the 48 needle assembly so that the cannula moved out of the case and entered the body (pierced the skin) of the user, and the flow path from the 49 reservoir to the user's skin is open to fluid flow or movement thereby delivering a portion of the medicament to the user (as shown in FIG. 11). FIG. 11 also shows that the 41 wedge progresses to the right so that an additional portion of the back of the 41 wedge is now visible to the user as a reducing portion of green and an increasing portion of red indicators thereby giving a visual delivery status to the user as the medicament is in the process of being delivered.

Figure 12:
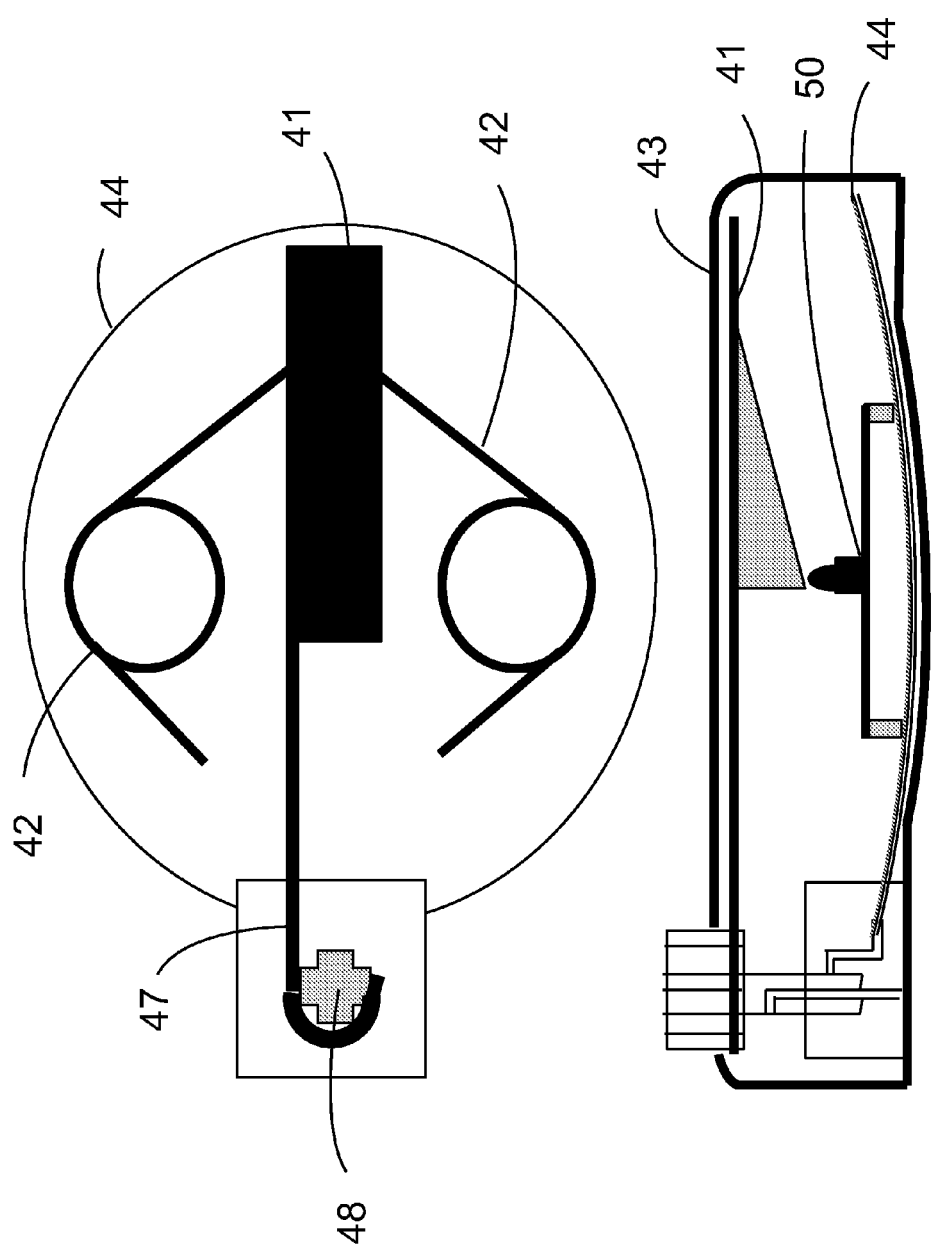
FIG. 12 illustrates a perspective view of an embodiment of a delivery device disclosed herein comprising a configuration with torsion springs, an emptied drug reservoir and a needle retracted.
Figure 13:
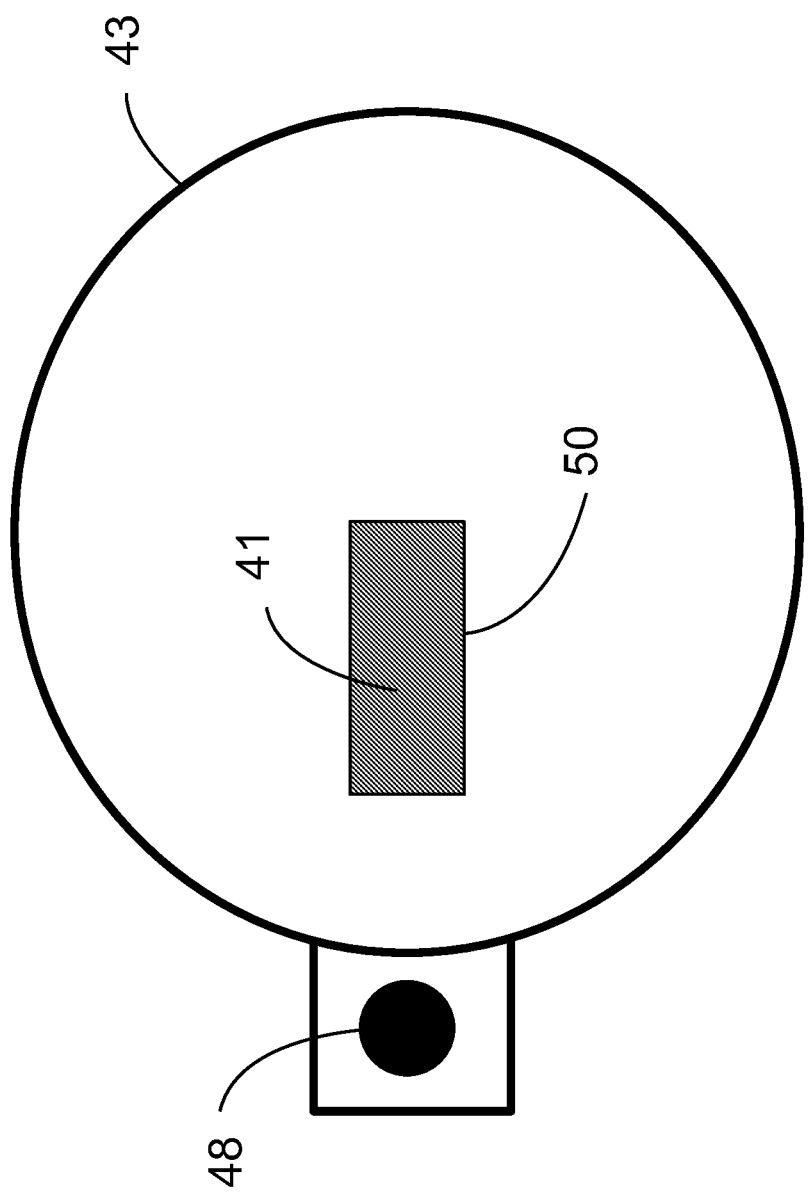
FIG. 13 illustrates another perspective view of an embodiment of a device disclosed herein (and shown in FIG. 12).

FIG. 12 shows an embodiment of the device/patch disclosed herein wherein delivery of the medicament is complete. 42 Torsion springs move the 41 wedge completely to the right and the 50 presser member has fully compressed the 49 reservoir thereby causing the desired dose of the medicament to leave the 49 reservoir. The 47 wedge extension causes the 48 needle assembly to rotate, closing the flow path and causing the cannula to be removed from the body/skin of the user. FIG. 13 shows the back of the 41 wedge member as red indicating to the user that medicament delivery is completed. Color combinations relating to indicator status are only exemplary and can vary as any of a range of colors.

For example, in yet another aspect of an embodiment of the delivery device or patch disclosed herein, user indicator status capabilities may be incorporated into the device. In one or more embodiments, indicator status information relating to any or all of medicament dose, appearance, flow, and delivery may be provided on a display panel or window on the backside of the inclined surface. Such a window provides the user with the capability to observe such indications. Additionally, particularly for persons who are visually impaired, certain status indicators, such as proper needle deployment, proper needle retraction, and completeness of medicament delivery may be provided in both a tactile and audible manner.

Figure 14:
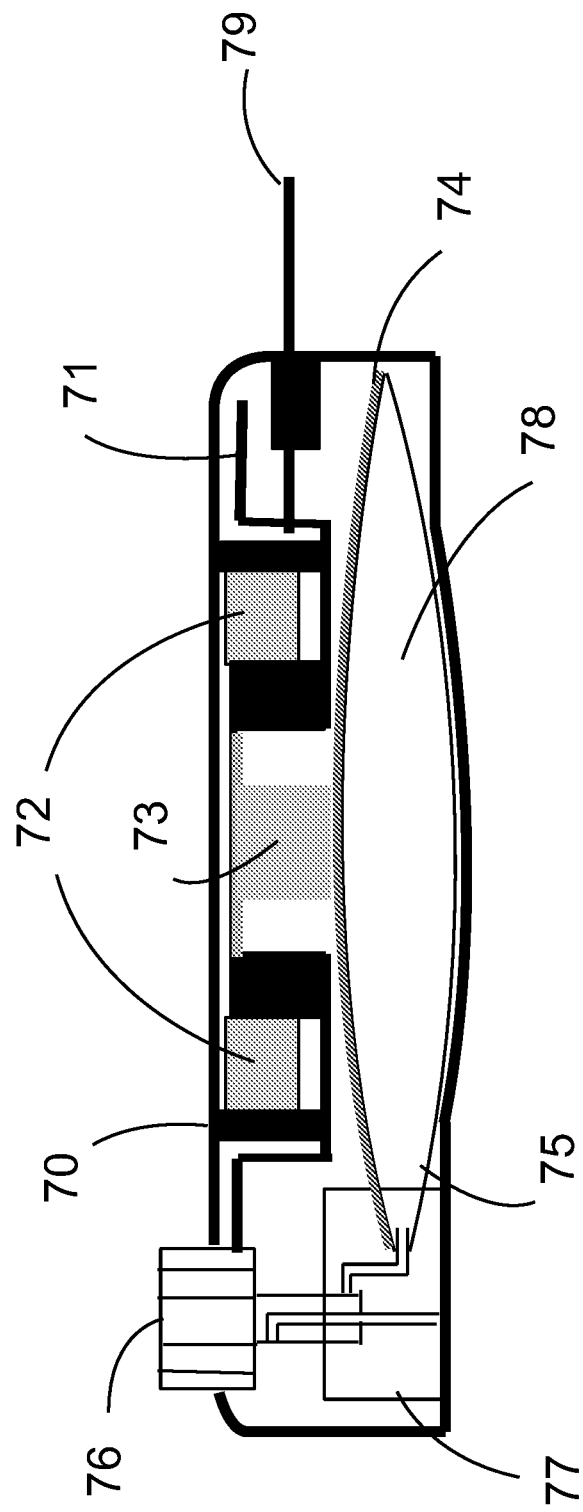
FIG. 14 illustrates a perspective view of an embodiment of a delivery device disclosed herein comprising a configuration with a spiral spring when the drug reservoir is full.

Alternative embodiments of the device disclosed herein are shown in FIGS. 14 through 17. The reservoir subsystem is essentially the same as described for FIGS. 8, 10 and 12. Fluid is held between an 75 inner biocompatible layer, a 74 flexible member with a similar biocompatibility layer, and an 70 outer case. The 76 needle assembly and fluid outlet assembly is also similar to that shown in prior Figures. In FIG. 14, a 72 watch spring is used as the source of mechanical force. As it rotates after the 79 pin is pulled, 71 rotating member drives 73 pushing member which is rigidly attached to 74 flexible upper member. As the 71 rotating member rotates, the 76 needle assembly is rotated to drive the needle downward and to open the fluid path, in a manner similar to that shown and described in FIGS. 8, 10, and 12, so that the medicament flows to the patient through the needle in the 76 needle assembly.

Figure 15:
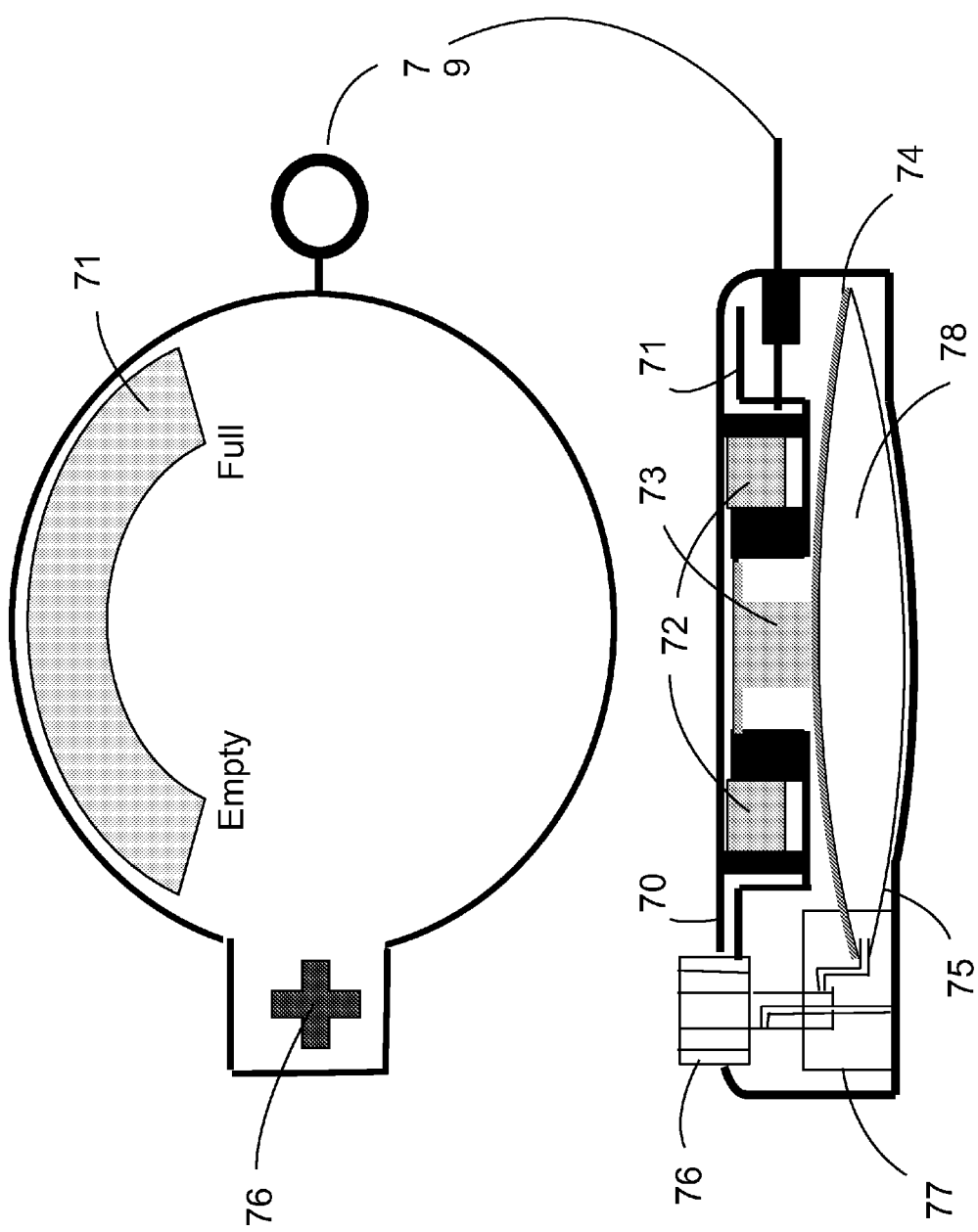
FIG. 15 illustrates another perspective view of an embodiment of a delivery device disclosed herein comprising a configuration with a spiral spring when the drug reservoir is full.

FIG. 15 shows an alternative prospective top view (from above) of the embodiment shown in FIG. 14 which shows the delivery status indicator markings on the outward facing surface of 71 rotating member. In this embodiment, the device is ready for use but has not yet been activated since activation 79 pin is still in place. The upper surface of the 71 rotating member, seen through the viewing window shows a green arc indicating the device is unused and full of medicament.

Figure 16:
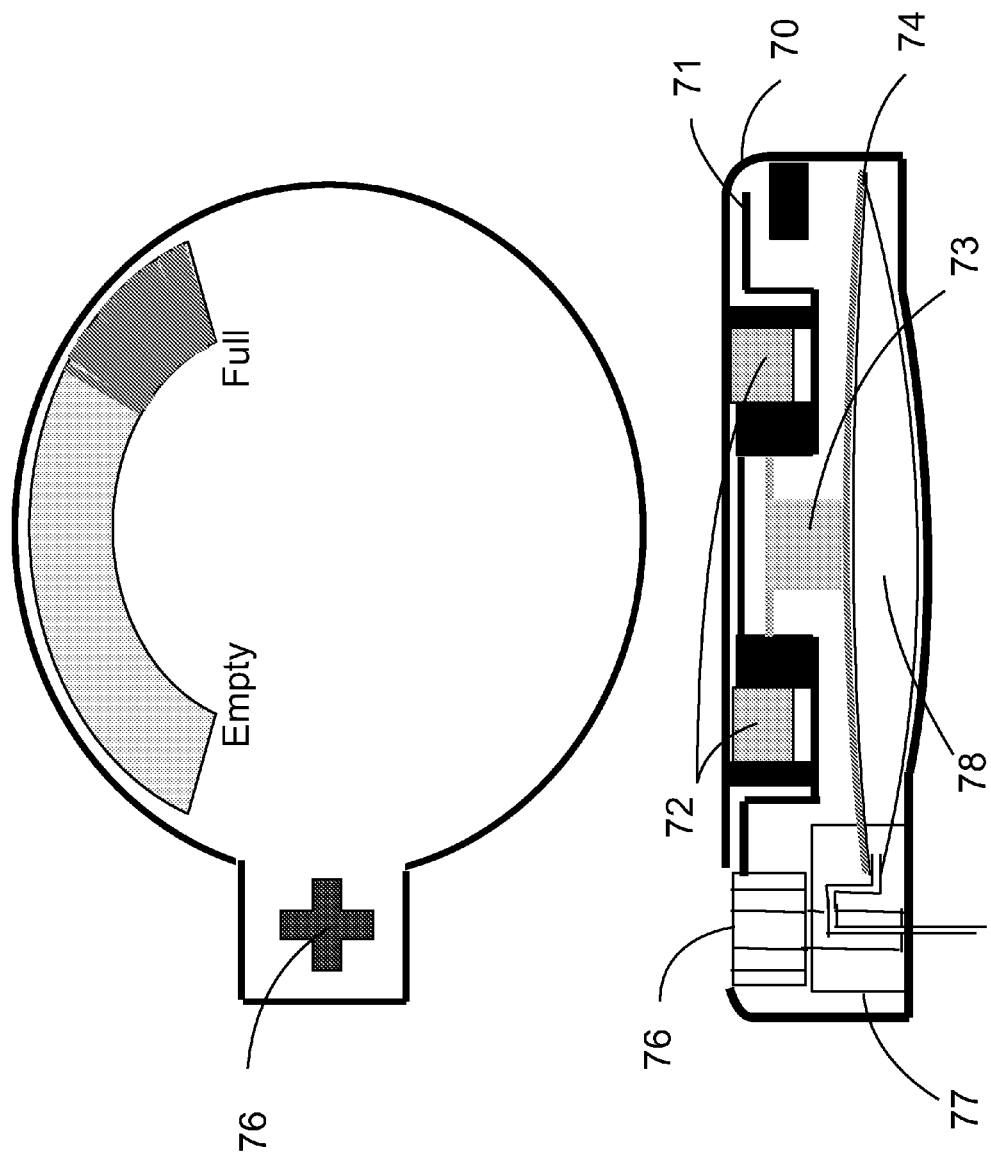
FIG. 16 illustrates perspective view of an embodiment of a delivery device disclosed herein comprising a configuration with a spiral spring when the drug reservoir is about half full and the needle is deployed.
Figure 17:
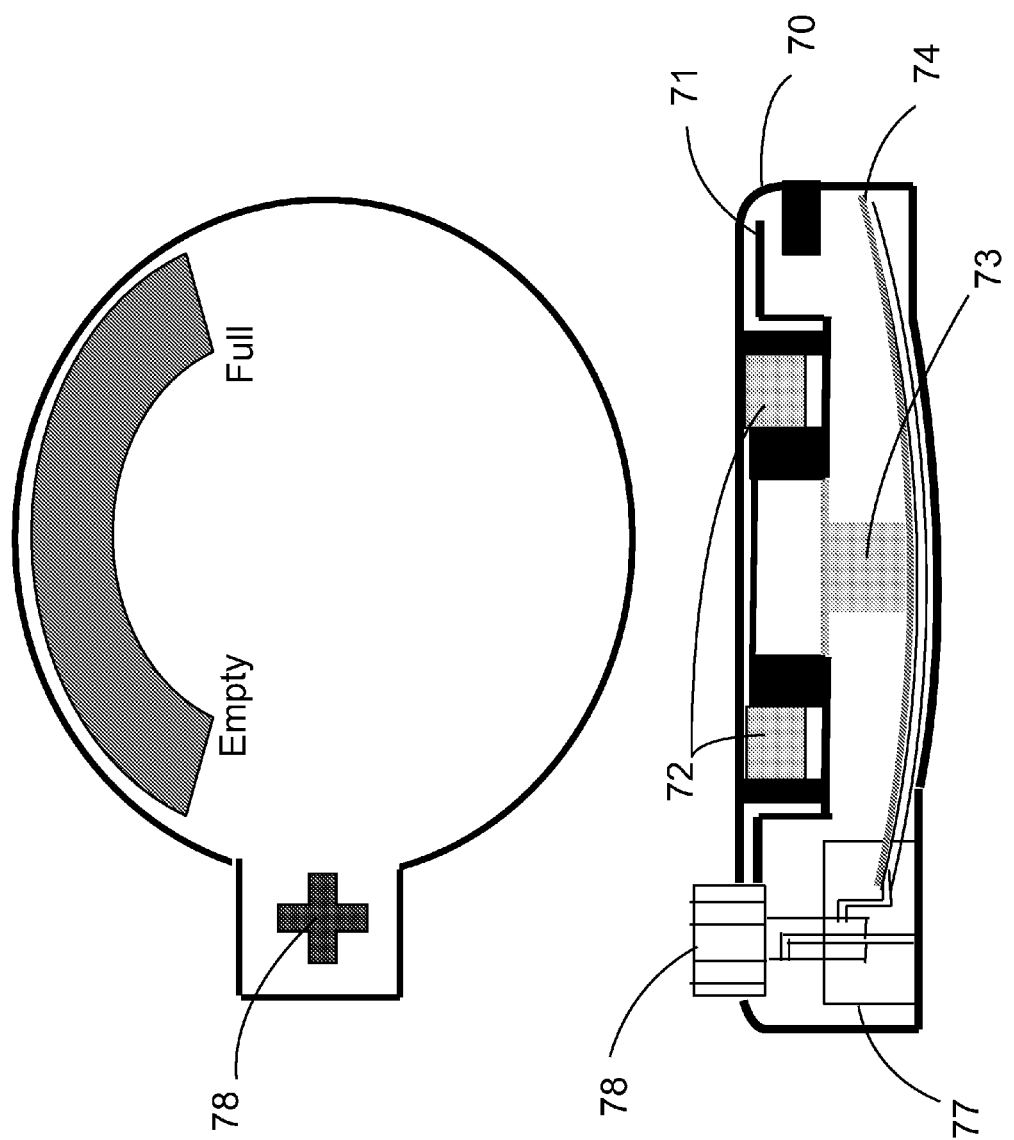
FIG. 17 perspective view of an embodiment of a delivery device disclosed herein comprising a configuration with a spiral spring when the drug reservoir is empty and the needle retracted.

FIG. 16 shows a device disclosed herein after the activation 79 pin is removed and the 72 driving spring is rotated through a portion of its rotational travel. In this embodiment of the device or patch disclosed herein, the ramp (inclined surface or wedge), in the form of a portion of the thread of a screw, is on the inner vertical surface of the 71 rotating member. The 73 pushing member follows the ramp and thereby presses the 78 reservoir to force medicament from the 78 reservoir. Furthermore, as the 71 rotating member rotates, the outer edge of the rotating member rotates the 76 needle assembly within 77 hub so that the needle moves from inside the device 70 housing to outside the device 70 housing thereby piercing the skin of the user. The flow path within the 76 needle assembly opens so that the medicament flows to the patient. The 71 rotating member rotates to make visible the indicator status information through the viewing window which indicates the device is delivering the medicament. A red section of the arc on the 71 rotating member appears through the window, in a manner similar to a familiar gas gauge in an automobile, providing an indication that the fluid is flowing and giving an approximation of the amount of medicament left to be delivered. A 72 spring continues to drive the delivery process to complete the delivery of the medicament as shown in FIG. 17. The 71 rotating member rotates as far as possible and the 73 pushing member fully compresses the 78 reservoir so that the entire dose of medicament is delivered. During the final several degrees of rotation of the 71 rotating member, it further rotates the 76 needle assembly thereby, through an action of a cam, for example, within the 76 needle assembly, drawing the needle back inside the device housing and closing the flow path from the 78 reservoir to the needle. This aspect of an embodiment of the device disclosed herein, provides a device design configuration precluding the possibility of inadvertent reuse of the device.

In other embodiments, the delivery device or patch disclosed herein may further be provided in a kit or set and may incorporate adjunctive elements and/or device members or components such as cams, screws, and/or a combination device disclosed herein, and/or the various components and/or members which make up the device such as, for example, without limitation, the device 43, 70 case or housing, the 10, 25, 49, 78 reservoir and/or reservoir walls, the inclined surface, the 24, 75 biocompatibility liner, the visual or audio indicator members, the viewing window, may be constructed and/or configured with materials such as, without limitation, poly-olefins such as polyethylene, thermoplastics such as polycarbonate and/or spring metals such as stainless steel as are known to those skilled in the art and are capable of performing in the required way.

The delivery device disclosed herein may incorporate reasonable design parameters, features, modifications, advantages, and variations that are readily apparent to those skilled in the art in the field of delivery devices.

While the invention herein disclosed has been described by means of specific embodiments and applications thereof, numerous modifications and variations could be made thereto by those skilled in the art without departing from the scope of the invention set forth in the claims.

What is claimed is:

1. A spring-driven drug delivery device comprising: a reservoir having an outer surface and an inner cavity configured to contain a fluid that comprises a medicament to be delivered to a body; a force transmission member that is moveable relative to said reservoir, wherein the force transmission member comprises an inclined surface; an inclined surface follower in contact with said inclined surface, wherein said inclined surface follower is coupled to said outer surface of said reservoir; a spring coupled to said force transmission member, wherein said spring exerts a spring force on said force transmission member, wherein said spring force comprises a horizontal force; and, a cannula connected by a flow path to said inner cavity of said reservoir, and configured to deliver said fluid into said body; wherein said spring force on said force transmission member generates motion of said force transmission member relative to said reservoir, wherein a slope of said inclined surface varies along said inclined surface to apply a force on said outer surface of said reservoir, and wherein said inclined surface follower is in contact with said inclined surface, such that said motion causes said inclined surface to move in a same linear direction as the horizontal force of the spring force, and such that said motion causes said inclined surface to move by, pressing on and sliding against said inclined surface follower, to exert said force on said outer surface of said reservoir, to generate a pressure on said reservoir and said fluid that causes said fluid to flow on said flow path to said cannula and into said body, to achieve a desired rate of delivery of said fluid as a function of time.

2. The spring-driven drug delivery device of claim 1, wherein said force transmission member comprises a wedge.

3. The spring-driven drug delivery device of claim 1, further comprising a flow resistor that limits a rate at which said fluid flows in said flow path.

4. The spring-driven drug delivery device of claim 1, wherein said force on said outer surface of said reservoir remains substantially constant throughout a portion of said motion of said force transmission member.

5. The spring-driven drug delivery device of claim 4, wherein
said spring force comprises a variation during said portion of said motion of said force transmission member; and
at a point of contact between said inclined surface and said inclined surface follower, said slope of said inclined surface changes during said portion of said motion of said force transmission member configured to compensate for said variation in said spring force and to generate a substantially constant force on said outer surface of said reservoir.

6. The spring-driven drug delivery device of claim 1, further comprising a cannula deployment assembly that extends said cannula into said body prior to delivery of the medicament and retracts said cannula after said delivery of the medicament.

7. The spring-driven drug delivery device of claim 6, wherein
said inclined surface is coupled to said cannula deployment assembly;
said motion of said force transmission member comprises a cannula extension motion, followed by a medicament delivery motion, followed by a cannula retraction motion.

8. The spring-driven drug delivery device of claim 1, further comprising a housing configured to be worn by a user on the user's skin, wherein said housing contains said reservoir, said force transmission member, and said spring.

9. The spring-driven drug delivery device of claim 8, wherein said housing is a patch having a height above said user's skin that is substantially smaller than a width and a length of said housing parallel to said user's skin.

10. The spring-driven drug delivery device of claim 1, wherein said reservoir comprises
a first reservoir comprising a rigid outer shell and an inner liner, wherein
said inner liner surrounds said inner cavity configured to contain said fluid that comprises said medicament;
said inner liner comprises a flexible area that is not coupled to said rigid outer shell and that separates said inner cavity from a secondary chamber within said first reservoir between said flexible area and said rigid outer shell;
a second reservoir containing an auxiliary fluid;
an auxiliary fluid flow path between said second reservoir and said secondary chamber of said first reservoir;
wherein said inclined surface follower applies force to said second reservoir, to cause said auxiliary fluid to flow into said secondary chamber, to apply force to said fluid in said inner cavity.

11. The spring-driven drug delivery device of claim 10, wherein said auxiliary fluid flow path comprises an auxiliary fluid flow restrictor that regulates a rate of flow of said auxiliary fluid into said secondary chamber.

12. The spring-driven drug delivery device of claim 11, wherein said auxiliary fluid has a higher viscosity than said fluid comprising said medicament.

13. A spring-driven drug delivery device comprising: a reservoir having an outer surface and an inner cavity configured to contain a fluid that comprises a medicament to be delivered to a body; a force transmission member that is moveable relative to said reservoir, wherein the force transmission member comprises an inclined surface; an inclined surface follower in contact with said inclined surface, wherein said inclined surface follower is coupled to said outer surface of said reservoir; means for exerting a force on said force transmission member, wherein said force on said force transmission member comprises a horizontal force; and, a cannula connected by a flow path to said inner cavity of said reservoir, and configured to deliver said fluid into said body; wherein said force on said force transmission member generates motion of said force transmission member relative to said reservoir, wherein a slope of said inclined surface varies along said inclined surface to apply a force on said outer surface of said reservoir, and wherein said inclined surface follower is in contact with said inclined surface, such that said motion causes said inclined surface to move in a same linear direction as the horizontal force of the spring force, and such that said motion causes said inclined surface to move by, pressing on and sliding against said inclined surface follower, to exert said force on said outer surface of said reservoir, to generate a pressure on said reservoir and said fluid that causes said fluid to flow on said flow path to said cannula and into said body, to achieve a desired rate of delivery of said fluid as a function of time.

14. The spring-driven drug delivery device of claim 13, further comprising means for extending said cannula into said body prior to delivery of the medicament and means for retracting said cannula after said delivery of the medicament.

15. The spring-driven drug delivery device of claim 13, further comprising means for transforming a varying amount of said force on said force transmission member into a substantially constant force of said outer surface of said reservoir.

* * * * *

UNITED STATES PATENT AND TRADEMARK OFFICE
CERTIFICATE OF CORRECTION

PATENT NO. : 9,907,904 B2
APPLICATION NO. : 15/490821
DATED : March 6, 2018
INVENTOR(S) : Burton H. Sage, Jr. et al.

Page 1 of 1

It is certified that error appears in the above-identified patent and that said Letters Patent is hereby corrected as shown below:

In the Claims

Column 15, Line 14, Claim 14, replace "said body prior to delivery of the medicament and means for retracting" with --said body prior to delivery of the medicament and retracting--.

Signed and Sealed this
Seventeenth Day of April, 2018

Andrei Iancu
*Director of the United States Patent and Trademark Office*